United States Patent
Pischel

(10) Patent No.: US 6,232,497 B1
(45) Date of Patent: May 15, 2001

(54) METHOD FOR PRODUCING ALKALI METAL AND ALKALINE EARTH METAL PYRUVATES

(75) Inventor: Ivo Pischel, Trostberg (DE)

(73) Assignee: SKW Trostberg Aktiengesellschaft, Trostberg (DE)

( * ) Notice: Subject to any disclaimer, the term of this patent is extended or adjusted under 35 U.S.C. 154(b) by 0 days.

(21) Appl. No.: 09/467,554

(22) Filed: Dec. 20, 1999

(30) Foreign Application Priority Data

Dec. 23, 1998 (DE) ............................................... 198 59 773
Jul. 28, 1999 (DE) ............................................... 199 35 306

(51) Int. Cl.$^7$ ................................................. C07C 59/149
(52) U.S. Cl. ............................................................. 562/577
(58) Field of Search ............................................. 562/577

(56) References Cited

U.S. PATENT DOCUMENTS

| | | | |
|---|---|---|---|
| 4,242,525 | * 12/1980 | Kiyoura et al. | 562/577 |
| 5,723,661 | * 3/1998 | Zimmermann et al. | 562/577 |
| 5,962,734 | * 10/1999 | Pischel | 562/577 |

OTHER PUBLICATIONS

Zuman et al., Chemical Abstracts, vol. 109, abstract No. 125314, 1988.*

* cited by examiner

*Primary Examiner*—Porfirio Nazario-Gonzalez
(74) *Attorney, Agent, or Firm*—Fulbright & Jaworski, LLP

(57) ABSTRACT

A method for producing alkali metal and alkaline earth metal pyruvates is disclosed, in which salts of organic acids or acidic organic keto or hydroxy compounds containing as cation one from the group comprising Li, Na, K, Rb, Cs, Mg, Sr and Ba, or mixtures of these salts, are reacted with pyruvic acid at a temperature ranging from −20 to +120°C., if necessary in the presence of a solvent or diluent. In this way, alkali metal and alkaline earth metal pyruvates of high purity are obtained, which can be largely anhydrous and have a very long shelf life. In addition, novel Rb, Cs, Sr and Ba pyruvates are disclosed. These pyruvates are used, for example, to enhance endurance and strength in the field of sport, as protective substances for body cells and tissues, and as food supplements. They are also used for technical applications.

16 Claims, No Drawings

METHOD FOR PRODUCING ALKALI METAL AND ALKALINE EARTH METAL PYRUVATES

This invention relates to a method for producing very pure and largely anhydrous pyruvates, new kinds of pyruvates, and the use thereof.

Salts of pyruvic acid (pyruvates) are known to have valuable physiological, therapeutic and dietetic properties. Pyruvates, especially calcium pyruvates, are used to enhance endurance and strength in the field of sport, and to reduce weight and body fat in the field of health care, where they are also used as protective substances for body cells and tissues (in particular for cardiovascular, hepatic, nephrotic, peritoneal and neuronal tissues), as a substance which inhibits the formation of free radicals and also serves as a free-radical scavenger in body cells and tissues (including synovial tissues). In addition, pyruvates are used as food supplements, wound-healing agents and for the treatment of kidney diseases (acute kidney failure and nephrolithiasis).

Calcium and magnesium pyruvates, in particular, have become established as harmless agents suitable for therapeutic purposes and as food supplements.

There are only two methods which have been disclosed so far as prior art for producing calcium pyruvates. According to the article published by K. Jowanowitsch in "Monatshefte" No. 6, pp. 467–476 (1885), tartaric acid in glycerin is dehydrated and decarboxylated to a glycidyl pyruvate, which subsequently reacts with lime in aqueous solution to form calcium pyruvate. As was established by proceeding the examples of this publication, this process does not result in the formation of calcium pyruvates but of polymeric pyruvic acid derivatives.

According to the French patent 1 465 432, calcium pyruvate is obtained by neutralizing pyruvic acid with calcium carbonate, hydroxide or oxide in water. The disadvantage of this method is the fact that only impure and unstable calcium pyruvates are obtained, which contain more than 2.5 mol water of crystallization and occur in the form of 2,2-dihyroxypropionate ions. These reaction products usually contain little calcium pyruvate and comparatively large quantities of by-products, since the pyruvic acid or pyruvate ions react by ways of aldol addition or aldol condensation to form acyclic or cyclic dimers and polymers of pyruvic acid. As one result they do not have a sufficiently long shelf life to be used as therapeutic agents or food supplements, or for special physical or solid-state applications. Among the acyclic compounds, special mention must be made of para-pyruvic acid (4-hydroxy-4-methyl-2-oxoglutaric acid) and its salts, and of the higher aldol addition products. As by-products oxalic and methyl succinic acid may also be formed.

By way of lactonization, ketalization and other reactions, the acyclic pyruvic acid polymers can form cyclic compounds such as 2-hydroxy-2-methyl-4-oxoglutaric acid-5-lactone and derivatives of trimesic acid, isophthalic acid and pyran tricarboxylic acid (Beilstein, Hauptwerk Vol. 3, pp. 608–613; 1. Ergänzungswerk, pp. 217–219; 2. Ergänzungswerk, pp. 393–401; 3. Ergänzungswerk, pp. 1146–1156; 4. Ergänzungswerk, pp. 1505–1510). These by-products can be formed in a similar way during storage of calcium pyruvates containing more than 2.5 mol of water of crystallization.

Calcium pyruvates disclosed in the prior art are thus unsuitable for therapeutic uses (as free-radical scavengers, for cell protection, obesity, etc.) or as a food supplement, because during production and storage of these pyruvates by-products and decomposition products of pyruvic acid and its salts are formed which can be physiologically incompatible or even toxic. For the same reasons, the specifications for their preparation cannot be transferred to other alkaline earth metals.

Because of the formation of by-products during the production of alkali metal and alkaline-earth metal pyruvates according to prior art techniques until now the syntheses of rubidium or cesium pyruvate was not possible (cf. G. Gattow, W. Rach, Z. anorg. allg. Chem. 592 (1988), 160–164). Strontium and barium pyruvate, likewise, either cannot be prepared by prior art techniques, or else are not sufficiently pure.

Methods for preparing sodium and potassium pyruvates are also state of the art, but the resulting pyruvates are usually impure and therefore unstable and of low storage stability.

The object of this invention was thus to develop a method for producing alkali metal and alkaline earth metal pyruvates which does not have the aforementioned disadvantages of the prior art but yields products which have a long shelf life, are of high purity and contain a minimum of toxicologically harmful by-products.

This object was established according to the invention by reacting salts of acidic organic compounds selected from organic acids such as carboxylic acids or of acidic organic keto or hydroxy compounds containing a cation selected from the group comprising Li, Na, K, Rb, Cs, Mg, Sr and Ba, or mixtures of these salts, with pyruvic acid at a temperature ranging from −20 to +120° C., if necessary in the presence of a diluent or solvent.

Surprisingly, it was found that in this way high-purity alkali metal and alkaline earth metal pyruvates can be prepared, which have little water of crystallization and/or are largely anhydrous. The alkali metal and alkaline earth metal pyruvates obtained have a low percentage of by-products, especially of para-pyruvates. Preferably, the para-pyruvate content is $\leq 0.8\%$, more preferably $\leq 0.2\%$. Alkali metal and alkaline earth metal pyruvates prepared in this way are also thermostable and satisfy the requirement of a very long shelf life. The extent to which this applies was surprising, because pyruvic acid is a relatively unstable compound and because hitherto-known alkali metal and alkaline earth metal pyruvates decompose to dimeric and polymeric derivatives of pyruvic acid. It was found in addition that the alkali metal and alkaline earth metal pyruvates disclosed in the invention exhibit valuable biological, medical and/or interesting physical or solid-state properties.

According to the method of this invention, therefore, defined alkali metal and alkaline earth metal salts of organic acids or acidic organic keto or hydroxy compounds are reacted with pyruvic acid at a temperature ranging from −20 to +120° C., preferably +10 to +60° C. Suitable organic acids include, eg, aliphatic monocarboxylic acids which may be substituted, eg, with OH—, CO—, CN—, Cl— or Br groups, and/or may be unsaturated. Formic acid, acetic acid, propionic acid, butyric acid and lactic acid are examples of such monocarboxylic acids. For the method of the invention, use can also be made of aliphatic di- and tricarboxylic acids which may be unsaturated and/or substituted, eg, with OH— groups. Citric acid, tartaric acid, succinic acid, maleic acid, fumaric acid and malic acid are examples of such acids. Instead of organic acids, it is also possible to use acidic organic keto or hydroxy compounds, for example ascorbic acid. These organic salts can be used in the anhydrous form, as hydrates or as wet products.

According to the method of the invention, the pyruvic acid, too, can be used optionally in the anhydrous form, as an aqueous solution, or dissolved in a solvent or diluent. The invention additionally provides for the production of the pyruvic acid as an intermediate, for example by reacting an alkali metal pyruvate such as sodium or potassium pyruvate with an inorganic acid such as sulfuric or hydrochloric acid at a temperature ranging from −20 to +90° C., preferably −10 to +60° C.

Suitable solvents or diluents for the method of the invention are water and/or organic solvents such as alcohols (methanol, ethanol, isopropanol, cyclohexanol), ethers (diethyl ether, tetrahydrofuran, 1,4-dioxane), ketones (acetone, methylethyl ketone, cyclohexanone), esters (methyl acetate, ethyl acetate, ethyl formate), organic acids (formic, acetic, propionic, lactic and pyruvic acids), nitriles (acetonitrile), aliphatic (pentane, hexane, cyclohexane) and aromatic hydrocarbons (toluene). It is also quite possible, however, to react the organic salts with pyruvic acid in the absence of solvents or diluents.

The ratio of organic alkali metal or alkaline earth metal salt to pyruvic acid can be varied within wide limits, although it has proved to be especially advantageous if the organic salts and pyruvic acid are reacted in stoichiometric or approximately stoichiometric ratios, eg, where the molar ratio of metal salt and pyruvic acid is about 1.2–0.8:1 (in the case of alkali metal salts) and about 0.6–0.4:1 (in the case of alkaline earth metal salts).

The method of the invention is largely unproblematic to carry out, and can be conducted using standard techniques and familiar technical apparatus such as kneaders, mixers, blade dryers and agitating vessels.

In this manner a high yield (>95%) of the high-purity (>97%) alkali metal or alkaline earth metal pyruvates disclosed in the invention is obtained, without the need for any time-consuming purification steps. Of particular importance is the fact that the method according to the invention also allows the preparation of novel alkali metal and alkaline earth metal pyruvates, which are very pure, which have a very long shelf life and, in addition, can be largely anhydrous and have the following structural formula,

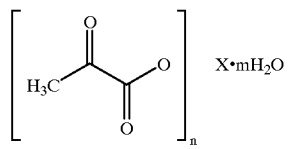

where
X=Rb, Cs, Sr, Ba
n=1, if X=Rb, Cs, or
n=2, if X=Sr, Ba, and
m=0–5.

According to the invention, the pyruvate anions in the claimed alkali metal and alkaline earth metal pyruvates are preferably present either as the 2-oxopropionate anion or as the 2,2-dihydroxypropionate anion.

As was established by means of IR-spectroscopic examination, the alkali metal and alkaline earth metal pyruvates produced according to the invention, which contain less than 2.5 mol water of crystallization, are obtained as the 2-oxopropionate ion.

By virtue of their high grade of purity and excellent storage stability, pyruvates produced according to the invention, especially Na, K and/or Mg pyruvates, are well suited for applications in the medical field and as food supplements. Pyruvates can be especially useful in the field of sport for enhancing endurance and strength, in the field of health care for reducing weight and body-fat, as a protective substance for body cells and tissues (especially cardiovascular, hepatic, nephrotic, peritoneal and neuronal tissue) and as a substance which inhibits the formation of free radicals and also serves as a free-radical scavenger in body cells and tissues (including synovial tissue), and for treating obesity and weight problems and as a food supplement. Additionally, the Rb, Cs, Sr and/or Ba pyruvates, in particular, are used in metrology and sensor technology, in photoelectrical technology and also, eg, in the medical field as contrast media and/or generally as bioactive substances. These alkali metal and alkaline earth metal pyruvates have been found to exhibit excellent solid-state properties, which makes them appear suitable for a large number of applications. For this reason, the range of uses is not yet complete.

This invention thus represents important overall progress with respect to pyruvate applications in the therapeutic and dietetic fields and in sports medicine. On the basis of the known prior art, it was not to be expected that pyruvates of the alkali metals rubidium and cesium and of the alkaline earth metals strontium and barium could be prepared as new chemical compounds, that with the proposed method a number of very pure alkali metal and alkaline earth metal pyruvates with excellent storage stability would become available, that during production of these pyruvates according to the method of the invention the pyruvic acid would not undergo any or only very limited condensation and decomposition reactions with formation of aldol adducts, that it would be possible to prepare the alkali metal and alkaline earth metal pyruvates mentioned from pyruvic acid produced as an intermediate, and that these pyruvates could be used without any subsequent purification. Last but not least, the alkali metal and alkaline earth metal pyruvate hydrates can contain 2,2-dihydroxypropionate ions instead of 2-oxopropionate ions.

The following examples illustrate the advantages of this invention in more detail.

EXAMPLES

Example 1

96 g (0.98 mol) of potassium acetate were added over a period of 1 hour at 40° C. to a solution of 88 g (1 mol) of pure pyruvic acid (99%) in 400 ml of ethyl acetate, and the mixture was stirred for 3 hours. The potassium pyruvate was subsequently vacuum-filtered and washed with 2×250 ml ethyl acetate. The yield of potassium pyruvate was 121 g (96% of the theoretical yield).

$C_3H_3O_3$ K: calculated: C 28.56%, H 2.46%, K 30.93%; found: C 28.5%, H 2.36%, K 30.3%; MP 178° C.; IR (KBr): 1700, 1610, 1390, 1350, 1175, 825; $^1$H-NMR (D$_2$O, 300 MHz): δ=2.41 (s, 3H, CH$_3$—CO), 1.60 (s, 3H, CH$_3$—C(OH)$_2$); content (HPLC): 100% K pyruvate, <0.2% para-pyruvate.

Example 2

At a temperature of 15–20° C. and over a period of 45 minutes, 64.3 g (0.49 mol) of 70% sulfuric acid were added dropwise to a suspension of 110 g (1 mol) of sodium pyruvate in 200 ml ethyl acetate. After 3 hours, the precipitated sodium sulfate was vacuum-filtered and washed with 2×40 ml ethyl acetate. The filtrate was heated to 35° C. Over a period of 30 minutes, 94.2 g ((0.96 mol) of potassium acetate were added. The suspension was stirred for a further 3 hours, after which the potassium pyruvate was vacuum-filtered and washed with 2×100 ml ethyl acetate. The product was dried to constant weight at 50° C. in a vacuum drying cabinet. The yield of potassium pyruvate was 115 g (95% of the theoretical yield).

Example 3

In a laboratory kneader, 44 g (1 mol) of pyruvic acid (99%) were added at 20° C. and over a period of 30 minutes to 49 g (0.5 mol) of potassium acetate, and the mixture kneaded for 2 hours. The potassium pyruvate, damp with acetic acid, was then dried at 50° C. and 12 mm Hg in a vacuum drying cabinet. The yield was almost quantitative (>99% of the theoretical yield).

Example 4

34 g (0.5 mol) of sodium formate were added at 40° C. over a period of 1 hour to a solution of 45.5 g (0.5 mol) of 98.7% pyruvic acid in 200 ml of ethyl acetate. The mixture was stirred for 3 hours at this temperature, cooled to 15° C. and then stirred for another hour. The sodium pyruvate was subsequently vacuum-filtered, washed with 2×100 ml of ethyl acetate and dried at 50° C. and 15 mbar. The yield of sodium pyruvate was 97% of the theoretical yield.

$C_3H_3O_3Na$: calculated: C 32.74%, H 2.75%, Na 20.89%; found: C 32.67%, H 2.64%; IR (KBr): 3443, 1628, 1179, 627; $^1$H-NMR ($D_2O$, 300 MHz): δ=2.43 (s, 3H, $CH_3$—CO), 1.62 (s, 3H, $CH_3$—$C(OH)_2$).

Example 5

82 g (1 mol) of sodium acetate were added at 40° C. over a period of 30 minutes to a solution of 88 g (1 mol) of pure pyruvic acid (99%) in 400 ml ethyl acetate, and the mixture was stirred for 2 hours. The sodium pyruvate was then vacuum-filtered at 25° C. and washed with 2×150 ml ethyl acetate. The product was dried to constant weight at 50° C. in a vacuum drying cabinet. The yield of sodium pyruvate was 94% of the theoretical yield.

Example 6

98.14 g (1 mol) of potassium acetate were added at 40° C. over a period of 30 minutes to a solution of 88 g (1 mol) of pure pyruvic acid (99%) in 400 ml ethyl acetate, and the mixture was stirred for 3 hours. The potassium pyruvate was then vacuum-filtered at 20° C., washed with 2×150 ml ethyl acetate and dried at 50° C. and 15 mbar. The yield of potassium pyruvate was 95% of the theoretical yield.

Example 7

5 g (33.9 mmol) rubidium acetate were added at RT over a period of 10 minutes to a solution of 3 g (34 mmol) of pure pyruvic acid (99%) in 40 ml dioxan and 0.1 g water, and the mixture was stirred for 3 hours. The rubidium pyruvate was then vacuum-filtered at 20° C., washed with a little dioxan, and dried at 50° C. and 15 mbar. The product, which was obtained in a yield of 85%, was strongly hygroscopic.

$C_3H_3O_3$ Rb: IR(KBr): 3436, 1627, 1354, 1179, 626; $^1$H-NMR ($D_2O$, 300 MHz): δ=2.41 (s, 3H, $CH_3$—CO), 1.60 (s, 3H, $CH_3$—$C(OH)_2$); content (HPLC): 89.5% Rb pyruvate, 0.8% para-pyruvate.

Example 8

25.5 g (0.25 mol) of lithium acetate were added at 20° C. over a period of 10 minutes to a solution of 22 g (0.25 mol) of pure pyruvic acid (99%) in 100 ml water, and the mixture was stirred for 1.5 hours. The lithium pyruvate was then dissolved by adding water at 60° C., the solution boiled down in a rotary film evaporator, and the product dried at 50° C. and 15 mbar to remove residual dampness.

$C_3H_3O_3$ Li: calculated: C 32.17%, H 4.50%, Li 6.20%; found: C 32.40%, H 4.40%; IR (KBr): 2995, 1603, 1144; $^1$H-NMR ($D_2O$, 300 MHz): δ=2.36 (s, 3H, $CH_3$—CO), 1.49 (s, 3H, $CH_3$—$C(OH)_2$).

Example 9

5 g (26 mmol) of cesium acetate were added at 20° C. over a period of 10 minutes to a solution of 2.3 g (26.3 mmol) of pure pyruvic acid (99%) in 50 ml dioxan, and the mixture was stirred for 21 hours. The cesium pyruvate was then vacuum-filtered, washed with a little dioxane and dried to constant weight at 50° C. and 15 mbar.

$C_3H_3O_3$ Cs: calculated: C 16.38%, H 1.37%, Cs 60.42%; found: C 16.49%, H 1.38%; IR (KBr): 3446, 1625, 1177, 625; $^1$H-NMR ($D_2O$, 300 MHz): δ=2.41 (s, 3H, $CH_3$—CO), 1.60 (s, 3H, $CH_3$—$C(OH)_2$).

Example 10

7.4 g (50 mmol) strontium acetate were added at 20° C. over a period of 10 minutes to a solution of 8.8 g (100 mmol) of pure pyruvic acid (99%) in 50 ml diethyl ether, and the mixture was stirred for 21 hours. The strontium pyruvate was then vacuum-filtered, washed with a little diethyl ether and dried to constant weight at 50° C. and 15 mbar.

IR (KBr): 3426, 1711, 1626, 1407, 1358, 1192, 981, 838, 745; $^1$H-NMR ($D_2O$, 300 MHz): δ=2.41 (s, 3H, $CH_3$—CO), 1.60 (s, 3H, $CH_3$—$C(OH)_2$).

Example 11

12.8 g (50 mmol) barium acetate were added at 20° C. over a period of 10 minutes to a solution of 8.9 g (100 mmol) of pure pyruvic acid (99%) in 50 ml dioxane, and the solution was stirred for 21 hours. The barium pyruvate was then vacuum-filtered, washed with a little dioxane and dried to constant weight at 50° C. and 15 mbar.

IR (KBr): 3405, 1706, 1618, 1399, 1356, 1189, 633; $^1$H-NMR ($D_2O$, 300 MHz): δ=2.41 (s, 3H, $CH_3$—CO), 1.60 (s, 3H, $CH_3$—$C(OH)_2$).

What is claimed is:

1. A method of preparing alkali metal and alkali earth metal pyruvates comprising:

reacting pyruvic acid with at least one acidic organic compound selected from the group consisting of Li, Na, K, Rb, Cs, Mg, Sr and Ba salt of an acidic organic compounds selected from acidic and alkali organic keto or hydroxy compounds at a temperature ranging from −20° C. to 120° C., optionally in the presence of a diluent or solvent;

recovering the resultant Li, Na, K, Rb, Ls, Mg, Sr or Ba pyruvate; and preparing an agent containing at least one of said Li, Na, K, Rb, Cs, Mg, Sr and Ba pyruvate.

2. The method of claim 1, wherein the said acidic organic compound is an Li, Na, K, Rb, Mg, Sr or Ba acidic organic compound, the resultant pyruvate is an Li, Na, K, Rb, Mg, Sr or Ba pyruvate and the agent comprises said Li, Na, K, Rb, Mg, Sr or Ba pyruvate.

3. The method of claim 1, wherein an aliphatic monocarboxylic acid is used as acidic organic compound, which may be substituted and/or unsaturated.

4. The method of claim 1, wherein
an aliphatic di- or tricarboxylic acid is used as acidic organic compound, which may be unsaturated and/or substituted with —OH groups.

5. The method of claim 1, wherein
ascorbic acid is used as acidic organic compound.

6. The method according to claim 1, wherein
the reaction is conducted at a temperature ranging from 10 to 60° C.

7. The method to according to claim 1, wherein
an organic solvent and/or water is used as solvent or diluent.

8. The method of claim 7, wherein
alcohols, ethers, ketones, esters, organic acids, nitriles, aliphatic and aromatic hydrocarbons are used as organic solvent.

9. The method according to claim 1, wherein
the pyruvic acid and the organic salts are reacted in a stoichiometric or approximately stoichiometric ratio.

10. Pyruvate of the general formula

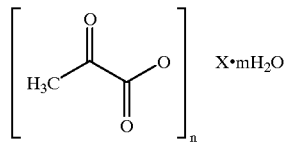

where
X=Rb, Cs, Sr, Ba
n=1, if X=Rb, Cs, or
n=2, if X=Sr, Ba, and
m=0–5.

11. The pyruvate of claim 10, wherein
the pyruvate anion is present as the 2-oxopropionate anion or as the 2,2-dihydroxypropionate anion.

12. A method of producing pyruvate-containing agents comprising:
reacting pyruvic acid with at least one of a sodium, potassium or magnesium acidic organic compound selected from acids and alkali organic keto or hydroxy compounds at a temperature ranging from −20° C. to 120° C., optionally in the presence of a diluent or solvent;

recovering the resultant sodium, potassium or magnesium pyruvate; and preparing an agent containing at least one of said sodium, potassium and magnesium pyruvate.

13. A method of producing pyruvate-containing agents comprising:
reacting pyruvic acid with at least one of a sodium, potassium or magnesium acidic organic compound selected from acids and alkali organic keto or hydroxy compounds at a temperature ranging from −20° C. to 120° C., optionally in the presence of a diluent or solvent; recovering the resultant sodium, potassium and magnesium pyruvates and preparing an agent containing at least one of said sodium, potassium and magnesium pyruvate.

14. A method of producing alkali metal and alkali earth metal pyruvates wherein
salts of acidic organic compounds selected from acids and acidic organic keto or hydroxy compounds containing a cation selected from the group comprising Li, Na, K, Rb, Cs, Mg, Sr and Ba or mixtures thereof, are reacted with pyruvic acid at a temperature ranging from −20 to +20° C., if necessary in the presence of a diluent or solvent, and the resulting pyruvates are recovered.

15. The method according to claim 14, wherein
the pyruvic acid is produced in situ.

16. The method of claim 15, wherein
the pyruvic acid is formed as an intermediate by reacting an alkali metal pyruvate with an inorganic acid such as sulfuric or hydrochloric acid.

* * * * *

UNITED STATES PATENT AND TRADEMARK OFFICE
CERTIFICATE OF CORRECTION

PATENT NO.    : 6,232,497 B1
DATED         : May 15, 2001
INVENTOR(S)   : Ivo Pischel It is certified that error appears in the above-identified patent and that said Letters Patent is hereby corrected as shown below:

<u>Column 8,</u>
Line 30, change "+20º C." to -- +120º C. --.

Signed and Sealed this

Twenty-first Day of October, 2003

JAMES E. ROGAN
*Director of the United States Patent and Trademark Office*